United States Patent [19]

Garret et al.

[11] Patent Number: 4,912,105
[45] Date of Patent: Mar. 27, 1990

[54] DERIVATIVES OF PHENOTHIAZINE AND THE COMPOSITIONS WHICH CONTAIN THEM

[75] Inventors: Claude Garret, Fontenay Sous Bois; Claude Guyon, Saint Maur des Fosses; Bernard Plau, Fresnes; Gérard Taurand, Creteil, all of France

[73] Assignee: Rhone-Poulenc Sante, Antony, France

[21] Appl. No.: 364,133

[22] Filed: Jun. 12, 1989

[30] Foreign Application Priority Data

Jun. 10, 1988 [FR] France ................. 88 07772

[51] Int. Cl.[4] ................. A61K 31/54; C07D 279/28
[52] U.S. Cl. ................. 514/226.2; 514/212; 514/225.9; 514/225.5; 540/599; 544/41; 544/42
[58] Field of Search ................. 544/41, 42; 540/599; 514/212, 225.2, 225.5, 226.2

[56] References Cited

U.S. PATENT DOCUMENTS 3,134,773  5/1964  Horclois et al. ................. 544/71

Primary Examiner—Richard L. Raymond

Attorney, Agent, or Firm—Stevens, Davis, Miller & Mosher

[57] ABSTRACT

Phenothiazine derivatives of formula

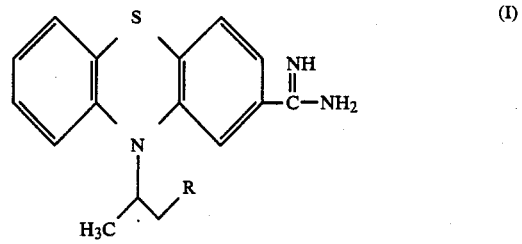

(I)

in which R represents $-NR_1R_2$ in which $R_1$ and $R_2$, which may be identical or different, are alkyl, hydroxyalkyl or acetyloxyalkyl radicals, or form, together with the nitrogen atom to which they are attached, a heterocycle containing 4 to 7 members which may be substituted by 1 or 2 alkyl, hydroxyalkyl or acetyloxyalkyl radicals, or R represents $-N^+R_1R_2R_3$ in which $R_1$ and $R_2$ are as defined above and $R_3$ is alkyl or phenylalkyl, their isomeric forms and their mixtures, and their salts, are useful in the field of antidiarrhetics.

8 Claims, No Drawings

DERIVATIVES OF PHENOTHIAZINE AND THE COMPOSITIONS WHICH CONTAIN THEM

This invention relates to phenothiazine derivatives and to their preparation and use.

In U.S. Pat. No. 3,112,310 phenothiazine amides of formula:

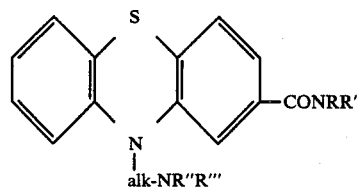

in which R is in particular a hydrogen atom, have been described as having activity on the central nervous system.

In Belgian Pat. No. 612,885 phenothiazine thioamides of general formula:

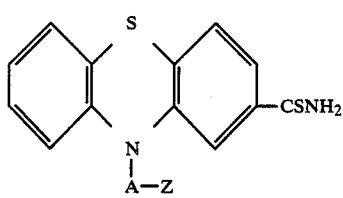

in which A is a carbon chain and Z is in particular a dialkylamino radical or a nitrogen containing heterocycle, have been described as neuroleptics, antiemetics, adrenolytics and anti-tubercular agents.

The present invention provides phenothiazine derivatives of formula:

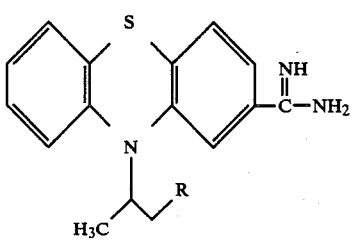

and their acid addition salts in which:
R represents
either a radical

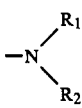 (IIa)

in which $R_1$ and $R_2$, which may be identical or different, each represent alkyl, hydroxyalkyl or acetyloxyalkyl radicals, or form, together with the nitrogen atom to which they are attached, a heterocyclic ring containing 4 to 7 members, which may be substituted by 1 or 2 alkyl, hydroxyalkyl or acetyloxyalkyl radicals,
or a radical

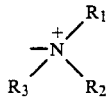 (IIb)

in which $R_1$ and $R_2$ are as defined above and $R_3$ represents alkyl or phenylalkyl. These new compounds show an affinity for opiate receptors of the Mu type, and have an antidiarrhetic activity without, however, any secondary effect on the central nervous system. In formula (I), it is to be understood that the alkyl radicals are straight-chain or branched and contain 1 to 4 carbon atoms each.

According to a feature of the invention, the products of formula (I) are obtained by the action of ammonia on an iminoether of formula:

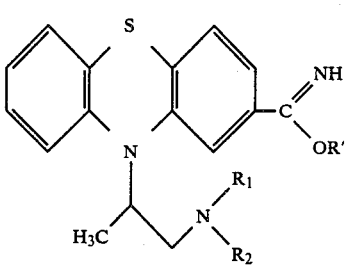

in which $R_1$ and $R_2$ are as defined as above and R' is alkyl of 1 to 10 carbon atoms, followed where necessary, when a product in which R is a radical of general formula (IIb) is desired, by the action of a compound of general formula:

$$R_3-X \qquad (IV)$$

in which $R_3$ is as defined above and X represents a halogen atom chosen from iodine, bromine or chlorine, or an alkylsulphonyloxy or phenylsulphonyloxy radical in which the phenyl radical is, if appropriate, substituted by one or more halogen atoms or alkyl or nitro radicals.

The reaction of ammonia on the iminoether is generally carried out in an organic solvent such as an alcohol (e.g. methanol, ethanol) or an ether (e.g. dioxane, "glyme", "diglyme"), at a temperature of between 0° and 50° C.

The action of the product of general formula (IV) takes place if necessary in a solvent such as an amide (dimethylformamide, hexamethylphosphorotriamide, or dimethylacetamide), a nitrile (acetonitrile), a ketone (acetone), a nitro derivative (nitromethane, nitrobenzene) or N-methylpyrrolidone, at a temperature of between 0° and 60° C.

The iminoether of general formula (III) may be obtained be treating, in an acid medium, a nitrile of general formula:

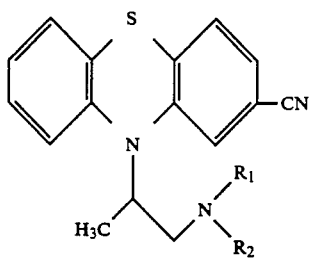

with an alcohol of general formula:

R'OH                                              (VI)

in which R' is defined as above.

In general, the reaction is carried out in the presence of hydrochloric acid, at a temperature of between −10° and 60° C. It is not essential to isolate the iminoether of general formula (III) to use it in the preparation of phenothiazine derivatives of general formula (I).

The nitrile of general formula (V) may be obtained according to the following reaction scheme:

1 to 4 carbon atoms (e.g. ethyl). The operating conditions are defined in more detail below in the examples.

The nitrile of general formula (XI) may be obtained as described in U.S. Pat. No. 2,877,224.

The isomers of products of formula (I) can be obtained by the use of known methods. This can be done, in particular, by preparation of the isomer of the phenothiazine derivative of general formula (IX) which is then converted to a phenothiazine derivative of general formula (I) by the methods described above.

The optically active derivative of the product of general formula (IX) is obtained, in particular, by preparation of the ester of a dibasic acid, formation of an optically active salt, separation of the isomers by crystallization, and saponification of the isomer obtained.

More particularly, the ester is obtained by means of the anhydride of a dibasic acid such as, for example phthalic anhydride, maleic anhydride or succinic anhydride. The salt is formed by addition of an optically active amine, for example (+)-1-phenylethylamine or (−)-1-phenylethylamine.

In the Examples which follow, the phenothiazine derivatives prepared from an alcohol of formula (IX) for which the rotatary power in solution in chloroform

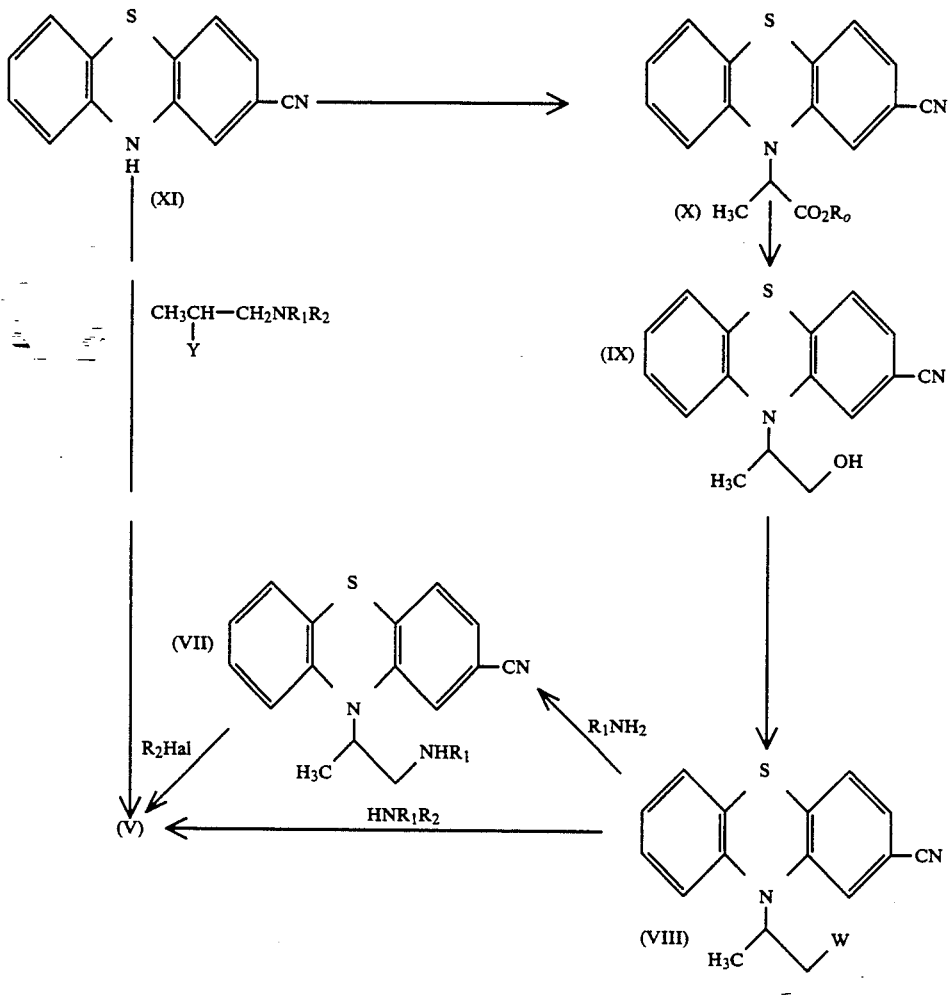

in which Y is a halogen atom chosen from chlorine, bromine or iodine or a p-toluenesulphonyloxy or methylsulphonyloxy residue, W is a p-toluenesulphonyloxy, methylsulphonyloxy or diaryloxyphosphoryloxy residue and $R_0$ is an alkyl radical containing is positive, are called series D; the phenothiazine derivatives prepared from an alcohol of formula (IX) for which the rotatary power in solution in chloro form is negative, are called series L.

The products of general formula (I) may be purified by chromatography or crystallization.

The phenothiazine derivatives of general formula (I) may be converted into acid addition salts by the action of an acid in an organic solvent such as an alcohol, a ketone, an ester, an ether or a chlorinated solvent. The salt precipitates, after concentration of the solution if necessary, and is separated off by filtration or decantation.

The addition salts with inorganic acids, such as the hydrochlorides, hydrobromides, sulphates, nitrates or phosphates, or organic acids such as the acetates, propionates, succinates, maleates, fumarates, methanesulphonates, p-toluenesulphonates or isethionates, or substitution derivatives of these compounds may be cited as pharmaceutically acceptable salts.

Phenothiazine derivatives of general formula (I) have a particularly useful antidiarrhetic activity because of their powerful affinity for the Mu receptors and their low toxicity.

They have, in fact, been shown to be active at concentrations of between 0.05 and 50 nM by the method of binding to tritiated [D-Ala, MePhe, Gly-ol] encephalin (tritiated DAGO) in guinea pig brain homogenates, suggested by the technique of Cotton, R. Kosterlitz H. W., et al., Br. J. Pharmac., 84, 927 (1985).

They have also been shown to be active in mice, by the technique for the determination of anti-diarrhetic activity suggested by the method of Niemegeers et al., Arz. Forsch., 22, 516 (1972). Their ED$_{50}$ is generally between 0.3 and 10 mg/kg by the subcutaneous route.

The acute toxicity dose (LD$_{50}$) of the compounds of formula (I) in mice is much higher than the effective dose. Their LD$_{50}$ is generally between 30 and 100 mg/kg s.c. or is even higher than 100 mg/kg s.c.

Of particular interest are the compounds of formula (I) in which R represents either a radical (IIa) in which $R_1$ and $R_2$, which may be identical or different, are alkyl radicals containing 1 to 2 carbon atoms, or form, together with the nitrogen atom to which they are attached, a heterocycle with 5 or 6 members which may be substituted by 1 or 2 methyl radicals, or R represents a radical (IIb) in which $R_1$ and $R_2$ are as defined above and $R_3$ represents an alkyl radical containing 1 to 2 carbon atoms.

The more especially active among these compounds are those in which R is as defined above, in the form of a mixture of isomers or in the D form.

The following products are especially interesting:
10-[1-(1-pyrrolidinyl)-2-propyl]-2-phenothiazinecarboxamidine;
10-[1-(2-methyl-2-pyrrolidinyl)-2-propyl]-2-phenothiazinecarboxamidine;
10-[1-(3,3-dimethyl-1-piperidyl)-2-propyl]-2-phenothiazinecarboxamidine;
10-[1-methyl-1-pyrrolidinio)-2-propyl]-2-phenothiazinecarboxamidine iodide.

The following examples illustrate the present invention.

EXAMPLE 1

Ammonia is bubbled into a solution of ethyl 10-[(2RS)-1-(1-pyrrolidinyl)-2-propyl]-2-phenothiazinecarboxamide hydrochloride (13.63 g) in absolute ethanol (150 cc) containing triethylamine (8.4 cc) for 4 hours. The reaction mixture is stirred for 24 hours at 25° C. The suspension obtained is then filtered, and the filtrate is concentrated to dryness at 50° C. under reduced pressure (5 mm Hg; 0.67 kPa) to give a yellow solid which is purified by chromatography on a column (height: 23 cm; diameter: 4 cm) of alumina by eluting with mixtures of methylene chloride and methanol at 95-5 (by volume) (750 cc) and 50-50 (by volume) (1500 cc) and collecting fractions of 125 cc. Fractions 8 to 11 are pooled and concentrated to dryness at 50° C. under reduced pressure (5 mg Hg; 0.67 kPa) to give 10-[(2RS)-1-(1-pyrrolidinyl)-2-propyl]-2-phenothiazinecarboxamidine hydrochloride (4.5 g) in the form of a yellow solid.

A solution of 10-[(2RS)-1-(1-pyrrolidinyl)-2-propyl]-2-phenothiazinecarboxamidine hydrochloride (4.3 g) in acetone (150 cc) is placed under reflux. The solution is filtered through fritted glass and the filtrate is primed by scratching. The mixture is stirred for 24 hours at 25° C. then centrifuged, and the solid is washed with iced acetone (10 cc) and dried at 60 C. under reduced pressure (1 mm Hg; 0.13 kPa) to give 3.35 g 10-[(2RS)-1-(1-pyrrolidinyl)-2-propyl]-2-phenothiazinecarboxamidine hydrochloride in the form of yellow crystals which melt at 228°–230° C.

Proton NMR (250 MHz, DMSO, δ in ppm, J in Hz). 1.65 (D, J=7, 3H, —CH$_3$); 1.7 (Cx, 4H, —CH$_2$—CH$_2$— of pyrrolidine); 2.53 (Mt in masked portion, N—CH$_2$— of pyrolidine); 2.86 (DD, J=13 and 6.5, 1H, 1H of NCH$_2$—); 3.04 (DD, J=13 and 6, 1H, 1H of N—CH$_2$—); 4.28 (Mt, J=7–6.5 and 6, 1H, N—CH); 6.95 to 7.3 (Mt, 4H, aromatics); 7.35 (limit AB, 2H, H at 3 and H at 4); 7.45 (S, 1H, —H at 1); 9.28 (Cx, about 3H,

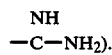

Infra-red spectrum (KBr), characteristic bands in cm$^{-1}$: 3240, 3070, 1665, 1595, 1525, 1460, 1420, 870, 830, 735.

Ethyl 10-[(2RS)-1-(1-pyrrolidinyl)-2-phenothiazinecarboximidate hydrochloride can be prepared in the following manner:

Hydrogen chloride gas is bubbled through a solution of 10-[(2RS)-1-(1-pyrrolidinyl)-2-phenothiazinecarbonitrile (25.16 g) in ethanol (150 cc) at 40° C. for 5 hours. The solution is concentrated to dryness at 50° C. under reduced pressure (30 mm Hg; 4 kPa) to give ethyl 10-[(2RS)-1-(1-pyrrolidinyl)-2propyl]-2-phenothiazinecarboximidate hydrochloride (38.7 g) in the form of a brown meringue.

The 10-[(2RS)-1-(1-pyrrolidinyl)-2-propyl]-2-phenothiazinecarbonitrile can be obtained in the following manner:

A mixture of 2-(2-cyano-10-phenothiazinyl)-(2RS)-1-propyl methanesulphonate (10 g) and pyrrolidine (11.6 cc) in toluene (50 cc) is brought to 90° C. while stirring for 24 hours. After cooling, the mixture is concentrated to dryness under reduced pressure (30 mm Hg; 4 kPa) at 40° C. and the residue is taken up in ethyl ether (200 cc) and a 4N aqueous solution of sodium hydroxide (15 cc). After stirring for 10 minutes, the organic phase is decanted and washed with a saturated aqueous solution of sodium chloride (3×25 cc), dried over magnesium sulphate, filtered and concentrated to dryness under reduced pressure (30 mm Hg; 4 kPa) at 20° C. The residual oil (11.3 g) is dissolved in a 0.05N aqueous solution of hydrochloric acid (60 cc). This solution is washed with ethyl ether (100 cc), then rendered alkaline with an excess of a N aqueous solution of sodium hydroxide and extracted with ethyl ether (100 cc). The organic phase is washed with a saturated aqueous solution of sodium chloride (50 cc), dried over magnesium sulphate, filtered and concentrated to dryness under reduced pressure (30 mm Hg; 4 kPa) at 20° C. The residual yellow oil (9.5 g) is purified on a column (height: 30 cm; diameter: 5.8 cm) of silica gel (0.04–0.063 mm) under a slight overpressure of nitrogen (40 kPa), eluting with a liter of a mixture of methylene chloride and methanol (95–5 by volume) and collecting fractions of 100 cc. Fractions 3 to 10 are pooled and concentrated to dryness under reduced pressure (30 mm Hg; 4 kPa) at 40° C. 10-[(2RS)-1-(1-pyrrolidinyl)-2-propyl]-2-phenothiazinecarbonitrile (5.45 g) is thus obtained in the form of a yellow oil.

The 2-(2-cyano-10-phenothiazinyl)(2RS)-1-propyl methanesulphonate can be obtained in the following manner:

Triethylamine (100 cc) and then, over 30 minutes, methanesulphonyl chloride (55.9 cc) are poured into a solution of 10-[(2RS)1-hydroxy-2-propyl]-2-phenothiazinecarbonitrile (120.5 g) in methylene chloride (1280 cc), cooled to a temperature of about 5° C., whilst stirring, and stirring is continued for 15 minutes while maintaining the temperature at 10°–15° C. The reaction mixture is diluted with distilled water (500 cc) at 5° C. and the organic phase is separated, washed with a saturated aqueous solution of sodium chloride (500 cc), dried over sodium sulphate, filtered and concentrated to dryness under reduced pressure (30 mm Hg; 4 kPa) at 40° C. The residual oil (164 g) is purified by chromatography on a column (height: 54 cm; diameter: 8.5 cm) of silica gel (0.2(sic)–0.063 mm), eluting with methylene chloride (4.4 liters) and then with a mixture of methylene chloride and methanol (99–1 by volume) (7 liters) and collecting fractions of 1 liter. Fractions 3 to 11 are pooled and concentrated to dryness under reduced pressure (30 mm Hg; 4 kPa) at 40° C. A yellow oil (153.5 g) is thus obtained, which is taken up in isopropyl ether (400 cc) under reflux. When cooled, a product crystallizes. Stirring is continued for 1 hour at a temperature of about 5° C. The solid formed is centrifuged, washed with iced isopropyl ether (2×50 cc) and dried at 30° C. under reduced pressure (30 mm Hg; 0.4 kPa). 2-(2-cyano-10-phenothiazinyl)(2RS)1-propyl methanesulphonate (131.6 g) thus obtained in the form of light yellow crystals which melt at 124° C.

The 10-[(RS)1-hydroxy-2-propyl]-2-phenothiazinecarbonitrile can be prepared in the following manner:

1,2-ethanedithiol (113 cc) is poured into a suspension of sodium borohydride (52 g) in tetrahydrofuran (1.4 liters), with stirring, in 15 minutes and at a temperature of about 20° C., and then a solution of ethyl (2RS)-2-(2-cyano-10-phenothiazinyl)propionate (296 g) in tetrahydrofuran (1.4 liters) is poured in 15 minutes under the same conditions. At the end of the addition, the reaction mixture is heated for 20 hours at a temperature of about 60° C. After cooling to a temperature of 5° C., a 4N aqueous solution of sodium hydroxide (1 liter) is poured in over 1 hour: a strong evolution of gas is observed. The reaction mixture is then poured into a mixture of a 4N aqueous solution of sodium hydroxide (1 liter) and methylene chloride (3 liters), while stirring. The organic phase is isolated and the aqueous phase is again extracted with methylene chloride (1 liter). The pooled organic phases are washed with a saturated aqueous solution of sodium chloride (2×1 liter), dried over magnesium sulphate, filtered and concentrated to dryness under reduced pressure (30 mm Hg; 4 kPa) at 30° C. The viscous orange oil (290 g) is purified on a column (height: 50 cm; diameter: 8.5 cm) of silica gel (0.2–0.063 mm), eluting successively with methylene chloride (3 liters), then a mixture of methylene chloride and methanol (97.5–2.5 by volume) (4 liters) and with a mixture of methylene chloride and methanol (95–5 by volume) (10 liters) and collecting fractions of 1 liter. Fractions 3 to 15 are pooled and concentrated to dryness under reduced pressure (30 mm Hg; 4 kPa) at 30° C. 10-[(2RS)1-hydroxy-2-propyl]-2-phenothiazinecarbonitrile (169.7 g) is thus obtained in the form of a yellow solid which melts at 123° C.

The ethyl (2RS)-2-(2-cyano-10-phenothiazinyl)propionate may be prepared in the following manner:

A solution of 2-phenothiazinecarbonitrile (224.5 g) in dimethylformamide (1 liter) is poured into a suspension of sodium hydride (24 g) in dimethylformamide (1 liter) at a temperature of about 25° C., whilst stirring and in 2 hours 30 minutes, then the mixture is stirred for a further 1 hour 15 minutes until evolution of gas has ended. The fine suspension obtained is poured, with stirring and at a temperature of about 25° C., in 4 hours 30 minutes into a solution of ethyl 2-chloropropionate (255 cc) in dimethylformamide (1 liter) and stirring is continued for 16 hours. Ethanol (100 cc) is then poured into the reaction mixture then the whole is poured onto a mixture of ice (2 kg) in distilled water (4 liters): a gum precipitates and then crystallizes. The solid formed is centrifuged, washed successively with distilled water (6×500 cc) and petroleum ether (2×500 cc) and dried in air. Ethyl (2RS)-2-(2-cyano-10-phenothiazinyl)propionate (296.5 g) is thus obtained in the form of khaki-colored crystals which melt at 117°–8° C., used as such in the following stage.

EXAMPLE 2

Hydrogen chloride gas is bubbled into a solution of D series 10-[1-(1-pyrrolidinyl)-2-propyl]-2-phenothiazinecarbonitrile (5 g) in absolute ethanol (100 cc) for 3 hours. The red reaction mixture is stirred for 16 hours at 25° C., purged by bubbling nitrogen through it for 2 hours, cooled to a temperature of about 0° C., and then saturated with ammonia by bubbling this through it for 6 hours. The mixture is then stirred at 25° C. for 16 hours, purged with nitrogen while warming to 40° C. for 1 hour and then concentrated to dryness of 50° C. under reduced pressure (30 mm Hg; 4 kPa). The residue (8.5 g) is purified by chromatography on a column (height: 30 cm; diameter: 3 cm) of alumina, eluting with methylene chloride (600 cc) then with mixtures of methylene chloride and methanol at 95–5 (600 cc), 90–10 (600 cc), 50–50 (2 liters) (by volume), collecting fractions of 60 cc. Fractions 15 to 35 are pooled and concentrated to dryness under reduced pressure (30 mm Hg; 4 kPa) to give a solid which is taken up in boiling isopropyl ether (200 cc). On cooling to 25° C., a yellow solid crystallizes. This solid is again dissolved in boiling acetonitrile (100 cc). On cooling, the product crystallizes. It is centrifuged, washed with acetonitrile (2×10 cc) then with ethyl ether (10 cc) and dried at 30° C. under reduced pressure (1 mm Hg; 0.13 kPa) to give D series 10-[1-(1-pyrrolidinyl)-2 -propyl]-2-phenothiazinecarboxamidine hydrochloride (4.5 g), in the form of a bright yellow powder which melts at 214°–216° C.

$[\alpha]_D^{20} = -42.2°$ (c=1.029%; methanol).

proton NMR (250 MHz, DMSO, δ in ppm, J in Hz). 1.65 (D, J=7, 3H, —CH₃); 1.7 (Cx, 4H, —CH₂—CH₂-of pyrrolidine); 2.53 (Mt masked,

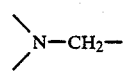

of pyrrolidine); 2.87 (DD, J=12.5 and 6.5, 1H, 1H of

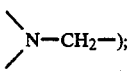

3.02 DD, J=12.5 and 6, 1H, 1H of

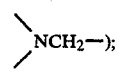

4.29 (Mt, J=7, 6.5 and 6, 1H,

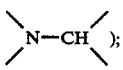

6.95 to 7.30 (Mt, 4H, aromatic); 7.35 (limit AB, 2H, —H at 3 and —H at 4); 7.45 (S, 1H, —H at 1); 9.20 (Cx, 3H,

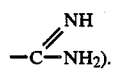

Infra-red spectrum (KBr), characteristic bands in cm⁻¹: 3250, 3060, 1670, 1595, 1525, 1460, 1415, 870, 820, 750.

The D series 10-[1-(1-pyrrolidinyl)-2-propyl]-2-phenothiazinecarbonitrile can be prepared in the following manner:

A mixture of D series 2-(2-cyano-10-phenothiazinyl)-1-propyl methanesulphonate 25.5 g) and pyrrolidine (29.6 cc) in toluene (260 cc) is heated for 52 hours at a temperature of about 90° C. The reaction mixture is concentrated to dryness under reduced pressure (30 mm Hg; 4 kPa) at 40° C. The residue is taken up in ethyl ether (500 cc) and extracted with a 2N aqueous solution of methanesulphonic acid (2×100 cc). The aqueous phase is rendered alkaline with washing soda (d=1.33) to pH 13 at a temperature of about 5° C. and successively extracted with distilled water (100 cc) and a saturated aqueous solution of sodium chloride (100 cc), dried over magnesium sulphate in the presence of carbon black 3S and filtered; the yellow filtrate is concentrated to dryness under reduced pressure (b 30 mm Hg; 4 kPa) at 40° C. The orange oil (18.2 g) thus obtained is purified by chromatography on a column (height: 45 cm; diameter: 4 cm) of silica gel (0.063-0.2 mm), eluting with a mixture of methylene chloride and methanol (97.5-2.5 by volume) (2.5 liters) and collecting fractions of 150 cc. Fractions 8 to 16 are pooled and concentrated to dryness under reduced pressure (30 mm Hg; 4 kPa) at 40° C. D series 10-[-1-(1-pyrrolidinyl)-2-propyl]-2-phenothiazinecarbonitrile (11.7 g) is thus obtained, in the form of a yellow oil.

$[\alpha]_D^{20} - 9.8° \pm 0.4°$ (1.1%; chloroform).

The D series 2-(2-cyano-10-phenothiazinyl)-1-propyl methanesulphonate may be prepared in the following manner:

Triethylamine (16.2 cc) is added with stirring, to a solution of D series 10-[1-hydroxy-2-propyl)phenothiazinecarbonitrile (20 g) in methylene chloride (200 cc) cooled to a temperature of about 5° C., then a solution of methanesulphonyl chloride (8.9 cc) in methylene chloride (89 cc) is poured in dropwise over 25 minutes, and stirring is continued for 50 minutes at a temperature of about 10° C. The reaction mixture is washed successively with distilled water (2×00 cc) and a saturated aqueous solution of sodium chloride (100 cc), dried over magnesium sulphate, filtered and concentrated to dryness under reduced pressure (30 mm Hg; 4 kPa) at 40° C. D series 2-(2-cyano-10-phenothiazinyl)-1-propyl methanesulphonate (25.8 g) is thus obtained in the form of an orange gum which is used without other purification for the syntheses following.

$[\alpha]_D^{20} = -23.1° \pm 0.4°$ (1.4%; chloroform).

The D series 10-1-hydroxy-2-propyl)-2-phenothiazinecarbonitrile can be prepared in the following manner:

(−)-2-(2-cyano-10-phenothiazinyl)-1-propyl 1-phenyl-(S)-ethylammonium phthalate (95.4 g) is added to a solution of 23.5 g of potassium hydroxide in 1150 cc ethanol under reflux and reflux is continued while stirring for 10 minutes. The reaction mixture is then poured into iced water (1 liter) and extracted with ethyl acetate (2 liters and then 500 cc). The combined organic phases are washed successively with a 0.1N aqueous solution of hydrochloric acid (2×500 cc), with a saturated aqueous solution of sodium bicarbonate (2×500 cc) and with a saturated aqueous solution of sodium chloride (500 cc), dried over magnesium sulphate, filtered and concentrated to dryness under reduced pressure (30 mm Hg; 4 kPa) at 40° C. The residual yellow solid (44 g) is taken up in isopropyl ether (200 cc) under reflux and the product crystallizes whilst warm. The mixture is allowed to return to a temperature of about 20° C. and the solid is centrifuged, washed with isopropyl ether (20 cc) and dried under reduced pressure (5 mm Hg; 0.7 kPa) at 20° C. D series 10-(1-hydroxy-2-propyl)-2-phenothiazinecarbonitrile (36.5 g) is thus obtained in the form of yellow crystals which melt at 135° C.

$[\alpha]_D^{20} = +13.1° \pm 0.5°$ (1.0%; chloroform).

The (−)-2-(2-cyano-10-phenothiazinyl)propyl and 1-phenyl-(1S)-ethylammonium phthalate can be prepared in the following manner:

A suspension of 10-[(2RS)1-hydroxy-2-propyl]-2-phenothiazinecarbonitrile (56.5 g) and phthalic anhydride (32.6 g) in anhydrous pyridine (100 cc) is refluxed for 6 hours, with stirring. After cooling, the reaction mixture is diluted with methylene chloride (500 cc), washed with distilled water (4×100 cc), dried over magnesium sulphate, filtered and concentrated to dryness under reduced pressure (30 mm Hg; 4 kPa) at 40° C. The residue is stirred with a N aqueous solution of hydrochloric acid (500 cc) and then decanted and dissolved in ethyl acetate (500 cc). The solution is washed with a N aqueous solution of hydrochloric (2×100 cc), acid then with an aqueous sodium chloride solution (100 cc). The organic phase is dried over magnesium sulphate, filtered and concentrated to dryness under reduced pressure (30 mm Hg; 4 kPa) at 50° C. A thick oil (102 g) containing [2-(2-cyano-10-phenothiazinyl)-(2RS)1-propyl]-2-oxycarbonylbenzenecarboxylic acid is thus obtained and used as such later.

The oil obtained above (102 g) which contains [2-(2-cyano-10-phenothiazinyl)-(2RS)1-propyl]-2-oxycarbonylbenzenecarboxylic acid is dissolved in ethyl acetate (500 cc) and a solution of (−)-1-phenyl-(1S)-ethylamine (24.2 g) in ethyl acetate (360 cc) is added, with stirring, at a temperature of about 20° C. After 2 days' stirring at a temperature of about 20° C., the solid formed is filtered off and dissolved in ethyl acetate (600 cc) under reflux. After cooling, the solid formed is centrifuged, washed with ethyl acetate (50 cc) and dried under reduced pressure (30 mm Hg; 4 kPa) at 40° C. (−)-2-cyano-10 -phenothiazinyl-propyl and 1-phenyl-(1S)-ethylammonium phthalate (44.2 g) is thus obtained in the form of light yellow crystals which melt at 154° C.

$[\alpha]_D^{20} = 21.5° \pm 0.6°$ (1%; chloroform).

EXAMPLE 3

A solution of D series 10-{1-[(2RS)-1-(2-methyl-1-pyrrolidinyl)-2-propyl}-2-phenothiazinecarbonitrile (0.52 g) in ethanol (10 cc) is saturated with hydrogen chloride gas by bubbling for 3 hours. The mixture is stirred for 12 hours at 25° C., purged by bubbling nitrogen through it for 2 hours and then saturated with ammonia by bubbling for 10 hours. The suspension is purged by bubbling nitrogen through it and filtered, and the filtrate is concentrated to dryness under reduced pressure at 50° C. (30 mm Hg; 3 kPa) to give a residue which is purified by chromatography on a column (height: 30 cm; diameter: 1.5 cm) of alumina, eluting with pure methylene chloride (200 cc), then with mixtures of methylene chloride and methanol at 90–10 (100 cc) and 50–50 (200 cc) (by volume), collecting fractions of 20 cc. Fractions 15 to 20 are pooled and concentrated to dryness under reduced pressure at 50° C. (30 mm Hg; 4 kPa) to give a golden-yellow solid (0.7 g) which is taken up in boiling isopropyl ether (10 cc). After scraping, crystallization begins. The suspension is brought to 25° C., with stirring, to give D series 10-[(2RS)-1-(2-methyl-1-pyrrolidinyl)-2-propyl]-2-phenothiazinecarboxamidine (0.53 g) in the form of yellow crystals which melt at about 75° C.

Proton NMR (250 MHz, DMSO, δ in ppm, J in Hz). 0.63 (D, J=6, 3H, —CH₃ of 2-methylpyrrolidinyl); 1.24 and 1.5 to 1.90 (2Mt, respectively 1H and 3H, —CH₂CH₂— of 2-methylpyrrolidinyl); 1.67 (D, J=7, 3H, CH₃); 2.08 (Mt, 1H, 1H of

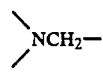

of 2-methylpyrrolidinyl); 2.25 (Mt, 1H, N-CH of 2-methylpyrrolidinyl); 2.27 (DD, J=13.5 and 5, 1H, 1H of

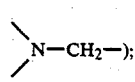

3.08 (Mt, 1H, 1H of

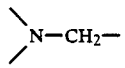

of 2-methylpyrrolidinyl); 3.35 (DD, J=13.5 and 6.5, 1H, 1H of

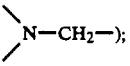

4.24 (Mt, J=7–6.5 and 5, 1H

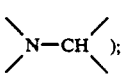

6.90 to 7.25 (Mt, 4H, aromatic); 7.32 (limit AB, 2H, —H at 3 and —H at 4); 7.43 (S, 1H, —H at 1); 9.20 (Cx, 4H

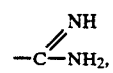

HCl).

Infra-red spectrum (KBr), characteristic bands in cm⁻¹: 3240, 3060, 1670, 1595, 1525, 1460, 1415, 870, 820, 750.

A solution of D series 2-(2-cyano-10-phenothiazinyl)-propyl methanesulphonate (6.8 g) in toluene (80 cc) and (2RS)-2-methylpyrrolidine (3.5 cc) is heated with stirring at 100° C. for 48 hours. After cooling to 25° C., the mixture is transferred into a separating funnel where it is washed with distilled water (2×200 cc) and brine (50 cc). The organic phase is dried over magnesium sulphate and filtered, and the filtrate is concentrated to dryness under reduced pressure (30 mm Hg; 4 kPa) to give a residue which is purified by chromatography on a column (height: 35 cm; diameter: 3.2 cm) of silica (0.2–0.06 mm), eluting with a mixture of cyclohexane and ethyl acetate 70–30 (by volume) (1 liter), collecting fractions of 60 cc. Fractions 11 to 14 are pooled and concentrated to dryness under reduced pressure (30 mm Hg; 4 kPa) to give 10-{1-[(2RS)-2-methyl-1-pyrrolidinyl]-2-propyl}-2-phenothiazinecarbonitrile, D series (0.5 g), in the form of a yellow oil.

Proton NMR (250 MHz, DMSO, δ in ppm, J in Hz). 0.73 (D, J=6, 3H, —CH₃ of 2-methylprrolidinyl); 1.24 and 1.5 to 1.9 (2Mt, respectively 1H and 3H, —CH₂— of 2-methylpyrrolidinyl); 1.62 (D, J=7.5, 3H, —CH₃); 2.09 (Mt, 1H, 1H of

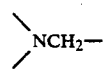

of 2-methylpyrrolidinyl); 2.27 (Mt, 1H, N—CH of 2-methylpyrrolidinyl); 2.37 (DD, J=13.5 and 5, 1H, 1H of 3.11 (Mt, 1H, 1H of 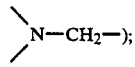

of 2-methylpyrrolidinyl); 3.32 (DD, J=13.5 and 7, 1H, 1H of 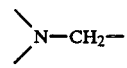);

4.10 (Mt, J=7.5-7 and 5, 1H, 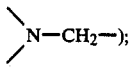);

6.95 to 7.25 (Mt, 4H, aromatic); 7.27 (D, J=7.5, 1H, —H at 4); 7.36 9DD, J=7 and 2, 1H, —H at 3); 7.57 (D, J=2, 1H, —H at 1).

EXAMPLE 4

Hydrogen chloride is bubbled into a solution of D series 10-[1-(3,3-dimethyl-1-piperidyl)-2-propyl]-2-phenothiazinecarbonitrile (8.3 g) in absolute ethanol (83 cc), for 5 hours at a temperature of about 45° C. The solution obtained is stirred for 16 hours at 25° C., purged by bubbling nitrogen through it, cooled to 0° C. and saturated with ammonia while maintaining the temperature at about 5° C. for 6 hours. The reaction mixture is stirred for 16 hours at 25° C., filtered, and the filtrate is concentrated to dryness yellow solid (12.5 g). This solid is taken up in methylene chloride (100 cc). The mixture is filtered and the filtrate is concentrated to dryness under reduced pressure (30 mm Hg; 4 kPa) at 50° C. to give D series 10-[(3,3-dimethyl-1-piperidyl)-2-propyl]-2-phenothiazinecarboxamidine hydrochloride (10 g) in the form of an amorphous yellow solid.

D series 10-[1-(3,3-dimethyl-1-piperidyl)-2-propyl]-2-phenothiazinecarboxamidine hydrochloride (7.8 g) is dissolved in boiling acetonitrile (400 cc). After cooling slightly to 70° C., crystallization develops. The suspension is stirred for 12 hours at 25° C. The solid is dewatered on fritted glass and dried at 60° C. under reduced pressure (1 mm Hg; 0.13 kPa) to give D series 10-[1-(3,3-dimethyl-1-piperidyl)-2-propyl]-2-phenothiazinecarboxamidine hydrochloride (4.49 g), in the form of golden-yellow crystals which melt at 256°-260° C.

$[\alpha]_D^{20} = -32°$ (c=1%; methanesulphonic acid 0.1N).

Proton NMR (250 MHz, DMSO, δ in ppm, J in Hz). 0.81 and 0.84 (2S, 6H, —CH₃ of 3,3-dimethylpiperidyl); 1.15 and 1.52 (2Mt, 2H for each, —CH₂— of dimethylpiperidyl); 1.65 (D, J=7, 3H, —CH₃); 2 (S, 2H, 

at 2-position of 3,3-dimethylpiperidyl; 2.15 and 2.42 (2Cx, each 1H, 

at 6-position of dimethylpiperidyl; 2.50 (DD in the masked part, 1H of );

2.92 (DD, J= 13.5 and 7.5, 1H, 1H of N—CH₂—); 4.32 (Mt, J=7.5-7 and 6.5, 1H, 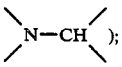);

6.95 to 7.25 (Mt, 4H, aromatic); 7.34 (limit AB, 2H, —H at 3 and —H at 4); 7.4 (S, 1H, —H at 1); 9.4 (Cx, 4H, $$-C\overset{NH}{\underset{}{\diagup}}_{NH_2}).$$

Infra-red spectrum (KBr), characteristic bands in cm⁻¹: 3240, 3060, 2975, 2940, 1665, 1595, 1525, 1460, 1415, 870, 810, 730.

The D series 0-[1-(3,3-dimethyl-1-piperidyl)-2-propyl]-2-phenothiazinecarbonitrile can be obtained in the following manner:

3,3-dimethylpiperidine (17 g) is added to a solution of 10.82 g D series 2-(2-cyano-10-phenothiazinyl)-propyl methanesulphonate in 40 cc toluene, and the solution obtained is heated at 90° C. for 24 hours. The reaction mixture is diluted with toluene (50 cc), washed with distilled water (3×50 cc), dried over magnesium sulphate and filtered and the filtrate is concentrated to dryness under reduced pressure (30 mm Hg; 4 kPa) at 50° C. to give a yellow syrup (11.4 g) which is purified by chromatography on a column (height: 48 cm; diameter: 3.8 cm) of silica (0.2-0.06 mm), eluting with a mixture of cyclohexane and ethyl acetate 80-20 (by volume) (1 liter) and collecting fractions of 125 cc. Fractions 3 to 7 are pooled and concentrated to dryness under reduced pressure (30 mm Hg; 4 kPa) at 20° C. to give D series 10-[1-(3,3-dimethyl-1-piperidyl)-2-propyl]-2-phenothiazinecarbonitrile (8.73 g), in the form of a yellow syrup. $[\alpha]_D^{20} = +23.7°$ (c=1%; methanol).

Proton NMR (250 MHz, CDCl₃, δ in ppm, J in Hz). 0.97 (S, 6H, —CH₃ of dimethylpiperidyl); 1.25 and 1.65 (2Mt, 2H for each, —CH₂— of dimethylpiperidyl); 1.64 (D, J=7, —CH₃); 2.08 (limit AB, 2H,

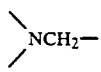

at 2-position of dimethylpiperidyl); 2.27 and 2.47 (2Cx, each 1H,

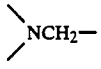

at 6-position of piperidyl); 2.59 (DD, J=13 and 6.0, 1H, 1H, of

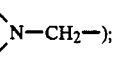

2.97 (DD, J=13 and 5.5, 1H, 1H of

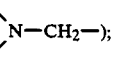

4.16 (Mt, J=7-6 and 5.5, 1H,

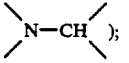

6.9 to 7.3 (Mt, 6H, (aromatic); 7.58 (S, 1H —H at 1).

Infra-red spectrum (CHCl₃), characteristic bands in cm⁻1: 2930, 2850, 2785, 2230, 1590, 1570, 1550, 1460, 1415, 870, 815.

EXAMPLE 5

Operating in a manner analogous to that described in Example 1 but starting with ethyl 10-[(1-dimethylamino) (2RS)-2-propyl]-2-phenothiazinecarboximidate hydrochloride (13.95 g), 10-[(1-dimethylamino) (2RS)-2-propyl]-2-phenothiazinecarboxamidine hydrochloride (3.52 g) is obtained in the form of yellow crystals which melt at 186°-88° C.

Proton NMR (400 MHz, DMSO D6, δ in ppm, J in Hz).

1.68 (D, J=7, 3H, —CH₃); 2.34 (S, 6H, —N(CH₃)₂); 2.81 (DD, J=12.5 and 6, 1H, 1H of

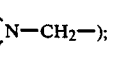

3.04 (DD, J=12.5 and 6.5, 1H, 1H of

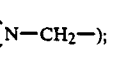

4.39 (Mt, J=7, 6.5 and 6, 1H,

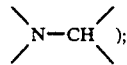

7 to 7.5 (Mt, 7H, aromatic; 9.5 (Cx, 4H,

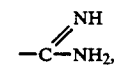

HCl).

Infra-red spectrum (KBr), characteristic bands in cm⁻1: 3340, 2000, 1670, 1630, 1590, 1460, 1525, 870, 820, 750, 740.

The ethyl 10-[(1-dimethylamino) (2RS)-2-propyl]-2-phenothiazinecarboximidate hydrochloride can be prepared in the following manner:

Working in a manner analogous to that described in Example 1, but starting from 10-[(1-dimethylamino) (2RS)-2-propyl]-2-phenothiazinecarbonitrile (9.28 g, ethyl 10-[(1-dimethylamino) (2RS)-2-propyl]-2-phenothiazinecarboximidate dihydrochloride (13.95 g) is obtained in the form of a brown meringue.

EXAMPLE 6

Working in a manner analogous to that described in Example 1, but starting from ethyl 10-[(1-dimethylamino) (2RS)-2-propyl]-2-phenothiazinecarboximidate dihydrochloride (11.92 g, 10-[(1-diethylamino[sic]) (2RS)-2-propyl]-2-phenothiazinecarboxamidine hydrochloride (7 g) is obtained in the form of a yellow powder which melts at 175°-180° C.

Proton NMR (400 MHz, DMSO D6, δ in ppm, J in Hz).

0.98 (T, J=7, 6H, —CH₂CH₃); 1.77 (D, J=7, 3H, —CH₃); 2.76 (Mt, 4H, —CH₂CH₃); 2.97 and 3.34 (2 Cx, each 1H,

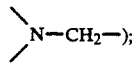

4.6 (Cx, 1H,

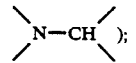

7 to 7.5 (Mt, 7H, aromatic); 9.35 and 9.56 (2 Cx, respectively 2H each,

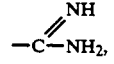

HCl).

Infra-red spectrum (KBr), characteristic bands in cm⁻1: 3240, 2840, 2790, 2660, 2480, 1675, 1630, 1590, 1460, 1525, 870, 750, 735.

The ethyl 10-[(1-dimethylamino) (2RS)-2-propyl]-2-phenothiazinecarboximidate dihydrochloride can be prepared in the following manner:

Working in a manner analogous to that described in Example 1 but starting with 10-[(1-dimethylamino)

(2RS)-2-propyl]-2-phenothiazinecarbonitrile (8.44 g), ethyl 10-[(1-dimethylamino) (2RS)-2-propyl]-2-phenothiazinecarboximidate dihydrochloride (11.92 g) is obtained in the form of an orange meringue.

EXAMPLE 7

Methyl iodide (0.036 g) is added to a solution of 10-[1-(1-pyrrolidinyl) (2RS)-2-propyl]-2-phenothiazinecarboxamidine hydrochloride (0.1 g) in dimethylformamide (1 cc) and the mixture is stirred for 16 hours at a temperature of about 20° C. The reaction solution obtained is poured into isopropyl ether (15 cc) and the oil formed is decanted, washed with isopropyl ether (15 cc) and again dissolved in a mixture of acetone and methanol (85–15 by volume) (12 cc). The preceding solution is poured dropwise, with stirring, into isopropyl ether (50 cc), and the yellow solid formed is filtered off and dried under reduced pressure (5 mm Hg; 0.67 kPa) at 50° C. 10-[1-(1-methyl-1-pyrrolidinio) (2RS)-2-propyl]-2-phenothiazinecarboxamidine iodide hydrochloride (0.11 g) is obtained in the form of a yellow powder which melts above 250° C., Proton NMR (250 MHz, DMSO D6, δ in ppm, J in Hz).

1.93 (D, J=7, 3H, —CH$_3$); 2.03 Mt, 4H, CH$_2$ of pyrrolidine); 3.01 (S, 3H, →NCH$_3$I$^-$); 3.33 and 3.57 (2 Mt, respectively 1H and 3H, →N+CH$_2$—, I$^-$ of pyrrolidine); 3.79 (DD, J=12.5 and 1.5, 1H, 1H of →N+CH$_2$—, I$^-$); (DD, J=12.5 and 9, 1H, 1H of →N+CH$_2$—,I$^{31}$); 4.86 *Mt, J=7.5, 7 and 1.5, 1H,

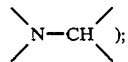

7.05 to 7.55 (Mt, 7H, aromatic); 8.8 to 9.5 (spread out Cx 4H,

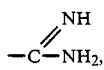

HCl),

Infra-red spectrum (KBr), characteristic bands in cm$^{-1}$: 3400, 2500, 1660, 1590, 1560, 1455, 1530, 1515, 860, 825, 750.

EXAMPLE 8

In manner analogous to that described in Example 9 (sic), but starting with D series 10-[1-(1-pyrrolidinyl)-2-propyl]-2-phenothiazinecarboxamidine hydrochloride (2 g) in dimethylformamide (20 cc) and with methyl iodide (0.75 g), D series 10-[1-(1-pyrrolidinio)-2-propyl]-2-phenothiazinecarboxamidine iodide hydrochloride (1.9 g) is obtained in the form of a yellow powder.

[α]$_D^{20}$= −33.4°±0.6° (c=0.856%; methanol)

Proton NMR (250 MHz, DMSO D6, δ in ppm, J in Hz).

1.94 D, J=7, 3H, —CH$_3$); 2.04 (Mt, 4H, —CH$_2$— of pyrrolidine); 3.01 (S, 3H, →N+CH$_3$I$^-$); 3.35 and 3.58 (2 Mt, respectively 1H and 3H, →N+CH$_2$—,I$^-$ of pyrrolidine); 3.81 (DD, J=14, 1H, 1H of →NCH$_2$—,I$^-$); 4.13 (DD, J=14 and 9, 1H, 1H of →N+CH$_2$—,I$^-$); 7.05 to 7.55 (Mt, 7H, aromatic); 8.96 to 9.34 (2 Cx, each 2H,

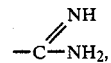

HCl).

Infra-red spectrum (KBr), characteristic bands in cm$^{-1}$: 3250, 3085, 1675, 1590, 1560, 1455, 1515, 865, 820, 750

EXAMPLE 9

In an analogous manner to that described in Example 7, but starting with 10-[1-(1-dimethylamino) (2RS)-2-propyl]-2-phenothiazinecarboxamidine hydrochloride (2.54 g) in dimethylformamide (15 cc) and with methyl iodide (0.99 g), 10-[(1-trimethylammonium) (2RS)-2-propyl]-2-phenothiazinecarboxamidine iodide (0.58 g) is obtained in the form of a greenish-yellow powder which melts at 248°–50° C.

Proton NMR (250 MHz, DMSO D6, δ in ppm, J in Hz).

1.90 (D, J=7, 3H, —CH$_3$); 3.12 (S, 9H, —N+(CH$_3$I$^-$); 3.77 (wide D, J=14, 1H, 1H of →N+CH$_2$—,I$^-$); 4.07 (DD, J=14 and 7.5, 1H, 1H of →N+CH$_2$—,I$^-$); 4.83 (Mt, J=7.5, 7 and 1, 1H,

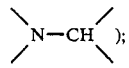

7.05 to 7.53 (Mt, 7H, aromatic).

Infra-red spectrum (KBr), characteristic bands in cm$^{-1}$: 3350, 2000, 3000, 1665, 1630, 1590, 1550, 1460, 875, 825, 755.

EXAMPLE 10

In a manner analogous to that described in Example 7, but starting with 10-[1-(1-diethylamino) (2RS)-2-propyl]-2-phenothiazinecarboxamidine hydrochloride (2.74 g) in dimethylformamide (15 cc), and with methyl iodide (0.99 g), 10-[(1-diethylmethylammonium) (2RS)-2-phenothiazinecarboxamidine iodide (0.38 g) is obtained, in the form of a pale green powder which melts at 254°–56° C.

Proton NMR (250 MHz, DMSO D6, δ in ppm, J in Hz).

1 to 1.20 (Mt, 6H, —CH$_2$CH$_3$); 1.95 D, J=7, 3H, —CH$_3$); 2.96 (S, 3H, →N+CH$_3$I$^-$); 3.42 (Mt masked, 4H, >N+(CH$_2$CH$_3$)$_2$I$^-$); 3.66 (wide D, J=15 and ≦1.5, 1H, 1H of →N>—CH$_2$−,I$^-$); 3.97 (DD, J=15 and 7.5, 1H, 1H of →N+CH$_2$—I$^-$); 4.82 (Mt, J=7.5, 7 and ≦1.5, 1H, >N—CH<); 7.05 to 7.5 (Mt, 7H, aromatic); 7.5 to 9 (spread-out Cx, 4H,

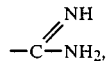

HCl).

Infra-red spectrum (KBr), characteristic bands in cm$^{-1}$: 3350, 2000, 1665, 1630, 1590, 1550, 1460, 1520, 870, 820, 755.

The present invention also provides pharmaceutical compositions which contain a phenothiazine derivative of formula (I) in association with a compatible and pharmaceutically acceptable adjuvant, diluent and/or coating. These pharmaceutical compositions may be used by the oral route.

Tablets, pills, powders or granules may be used as solid compositions for oral administration. In these compositions, the active product according to the invention (possibly associated with another pharmaceutically compatible product) is mixed with one or more diluents or inert adjuvants, such as sucrose, lactose or starch. These compositions may also contain substances other than diluents, for example a lubricant such as magnesium stearate.

Pharmaceutically acceptable emulsions, solutions, suspensions, syrups and elixirs containing inert diluents such as water or paraffin oil may be used as liquid compositions for oral administration. These compositions may also contain substances other than diluents, for example wetting, sweetening or flavouring products.

The compositions according to the invention are particularly useful in human therapeutics for their antidiarrhetic action.

Doses depend on the effect required and on the length of treatment; they are generally between 0.5 and 25 mg per day by the oral route for an adult.

In general, the doctor will determine the posology which he feels most appropriate in view of the age, weight and all other factors applying to the subject to be treated.

The following Example illustrates a composition according to the invention.

EXAMPLE

Tablets containing 1 mg of active product, and having the following composition, are prepared according to the usual technique:

D series 10-[1 -(2-methyl-1-pyrrolidinyl) (2RS)-2-propyl]-2-phenothiazinecarboxamidine
hydrochloride: 1.1 mg
Starch: 20 mg
Precipitated silica: 3.6 mg
Magnesium stearate 0.4 mg

We claim:

1. A phenothiazine derivative of formula:

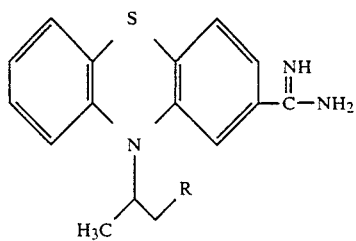

in which R represents
either a radical of formula:

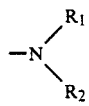

in which $R_1$ and $R_2$, which may be identical or different, each represent alkyl, hydroxyalkyl or acetyloxyalkyl radicals, or form, together with the nitrogen atom to which they are attached, a heterocyclic ring containing 4 to 7 members, which is unsubstituted or substituted by 1 or 2 alkyl, hydroxyalkyl or acetyloxyalkyl radicals,,
or a radical of formula:

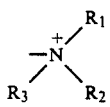

in which $R_1$ and $R_2$ are as defined above and $R_3$ represents alkyl or phenylalkyl, the aforesaid alkyl radicals and alkyl portions containing 1 to 4 carbon atoms each in a straight or branched chain, and its isomeric forms and their mixtures, and its said addition salts.

2. A phenothiazine derivative according to claim 1, in which R represents either $-NR_1R_2$ in which $R_1$ and $R_2$, which may be identical or different, each represent alkyl of 1 to 2 carbon atoms, or $R_1$ and $R_2$ form, together with the nitrogen atom to which they are attached, a heterocyclic ring with 5 or 6 members which is unsubstituted or substituted by 1 or 2 methyl radicals, or R represents $-N+R_1R_2R_3$ in which $R_1$ and $R_2$ are as defined above and $R_3$ represents alkyl of 1 or 2 carbon atoms, and its isomeric forms and their mixtures, and its acid addition salts.

3. A phenothiazine derivative according to claim 2, in the form of a mixture of isomers, or in the D form, and its acid addition salts.

4. A phenothiazine derivative according to claim 1 which is 10-[1-(1-pyrrolidinyl)-2-propyl]-2-phenothiazinecarboxamidine, and its isomeric forms and their mixtures, and its acid addition salts.

5. A phenothiazine derivative according to claim 1 which is 10-[1-(2-methyl-1-pyrrolidinyl)-2-propyl]-2-phenothiazinecarboxamidine, and its isomeric forms and their mixtures, and its acid addition salts.

6. A phenothiazine derivative according to claim 1 which is 10-[1-(3,3-dimethyl-1-piperidyl)-2-propyl]-2-phenothiazinecarboxamidine, and its isomeric forms and their mixtures, and its acid addition salts.

7. A phenothiazine derivative according to claim 1 which is 10-[1-(1-methyl-1-pyrrolidinio)-2-propyl]-2-phenothiazinecarboxamidine iodide, and its isomeric forms and their mixtures, and its acid addition salts.

8. A pharmaceutical composition containing at least one phenothiazine derivative according to claim 1, in association with a compatible and pharmaceutically acceptable diluent or adjuvant.

* * * * *